US00RE44340E

(19) United States
(12) Reissued Patent
Pyles

(10) Patent Number: US RE44,340 E
(45) Date of Reissued Patent: Jul. 2, 2013

(54) POWER SOURCE FOR AN IMPLANTABLE MEDICAL DEVICE

(76) Inventor: Stephen T. Pyles, Ocala, FL (US)

(21) Appl. No.: 13/466,416

(22) Filed: May 8, 2012

Related U.S. Patent Documents

Reissue of:
(64) Patent No.: 7,815,667
Issued: Oct. 19, 2010
Appl. No.: 11/458,885
Filed: Jul. 20, 2006

U.S. Applications:
(60) Provisional application No. 60/701,295, filed on Jul. 21, 2005.

(51) Int. Cl.
*A61N 1/39* (2006.01)
(52) U.S. Cl.
USPC ..... 607/1
(58) Field of Classification Search
USPC ..... 607/45, 1, 61
See application file for complete search history.

(56) References Cited

U.S. PATENT DOCUMENTS

| | | | | |
|---|---|---|---|---|
| 6,445,956 | B1 * | 9/2002 | Laird et al. | 607/61 |
| 7,074,432 | B2 | 7/2006 | Dasch et al. | |
| 2002/0087204 | A1 * | 7/2002 | Kung et al. | 607/61 |
| 2004/0176818 | A1 * | 9/2004 | Wahlstrand et al. | 607/45 |

OTHER PUBLICATIONS www.medtronic.com, Neurostimulation System Components and Implantation, Internet article, Sep. 5, 2001, 7 pages.
www.ans-medical.com, What is Spinal Cord Stimulation?, Internet article, 2005, 4 pages, Plano, Texas.
www.medtronic.com, Neurostimulators and Their Selection, Internet article, Sep. 5, 2001, 6 pages.
www.nagor.com, Gluteal Implants, Internet article, printed on Jul. 17, 2006.
www.nagor.com, Silicone Blocks, Internet article, printed on Jul. 17, 2006.

* cited by examiner

*Primary Examiner* — Carl H. Layno
*Assistant Examiner* — Jon-Eric C. Morales
(74) *Attorney, Agent, or Firm* — Gardner Groff Greenwald & Villanueva, P.C.

(57) ABSTRACT

A power source for an implantable medical device, such as a spinal cord stimulator, has a [controlled] *contoured* anterior surface. Preferably, the contoured anterior surface includes a layer of a biocompatible material, such as a polymer. Also preferably, the layer provides a contour generally conforming to the profile of a human buttock. Optionally, a cosmetic implant of generally substantially the same size and shape as the power source is implanted in the opposite buttock as the power source so as to create balance.

20 Claims, 3 Drawing Sheets

POWER SOURCE FOR AN IMPLANTABLE MEDICAL DEVICE

Matter enclosed in heavy brackets [ ] appears in the original patent but forms no part of this reissue specification; matter printed in italics indicates the additions made by reissue.

CROSS REFERENCE TO RELATED APPLICATIONS

This application claims priority to U.S. Provisional Patent Application Ser. No. 60/701,295, filed Jul. 21, 2005, which is hereby incorporated herein by reference in its entirety for all purposes.

TECHNICAL FIELD

The present invention relates generally to the field of surgical implants, and particularly to an improved power source for an implantable medical device, such as a spinal cord stimulator.

BACKGROUND OF THE INVENTION

Spinal cord stimulation is used to alleviate chronic pain by stimulating the central nervous system. Typically, a lead having a plurality, but usually four or eight, of electrodes is placed in the epidural space, in close proximity to the spinal cord. The lead is connected to a power source 2, which typically includes a disk-shaped or rectangular casing for housing a battery that is implanted in the patient's buttock 8, as shown in FIGS. 1 and 2. When activated, the power source delivers a pulse of energy to the electrodes, which in turn deliver a precise, mild electrical impulse to the spinal cord or to a peripheral nerve. The electrical impulses activate pain inhibitory mechanisms to block the pain signal from reaching the brain.

However, given that the typical power source is somewhat puck-like, the power source has a somewhat substantial size, including significant thickness. Typical power sources have a length and width or diameter of about 5-6 centimeters and a thickness of approximately 1.4 centimeters. Thus, some patients, including those who do not have much adipose tissue in their buttocks, may find that the power source creates a bulge with defined edges beneath the skin that is clearly visible, even under clothing.

Thus it can be seen that needs exist for an improvement to a power source for energizing implantable medical devices, such as a spinal cord stimulator, that minimizes the appearance of the power source beneath the patient's skin.

SUMMARY OF THE INVENTION

Advantageously, the present invention provides a power source for energizing implantable medical devices that minimizes the appearance of the power source implanted beneath the skin of one of the patient's buttocks. Preferably, the power source includes a contoured surface that generally conforms to the profile of the patient's buttock. Thus, the power source preferably does not create a bulge with defined edges beneath the skin that is clearly visible. Rather, the power source can enhance or blend with the natural contour of the patient's buttock. Optionally, an inert cosmetic implant can be implanted in the patient's other buttock to create balance.

In example forms, the present invention includes a housing for a power source for energizing an implantable medical device. Preferably, the power source has a contoured anterior surface, wherein the contoured surface can further include a layer of a biocompatible material such as a biocompatible polymer. Also preferably, the layer provides a contour generally conforming to a profile of a human buttock.

In another aspect, the invention includes an improvement for a power source for spinal cord stimulation. The improvement includes a layer of a biocompatible and inert material, such as a polymer, applied to an anterior surface of the power source for providing a contoured surface. Preferably, the layer is contoured to generally conform to the profile of the patient's buttock.

In still another aspect, the invention includes a kit for spinal cord stimulation. The kit includes a spinal cord stimulation lead, a power source, and an implant of substantially the same size and shape as the power source. Preferably, the power source is a battery having a contoured anterior surface for conforming to a contoured body part and formed of a biocompatible and inert material. Thus, the power source can be implanted into one of the patient's buttocks, and the implant can be implanted in the other so as to create a balance.

In still another aspect, the present invention includes a method of implanting a device into a human or animal subject. The method includes the steps of implanting a power source into one of a patient's buttocks at a predetermined height, depth, and lateral distance from the patient's spinal column and implanting a cosmetic implant of substantially the same size and shape as the power source into the other of the patient's buttocks at substantially the same height, depth, and lateral distance from the patient's spinal column as the implanted power source. The method can further include the step of connecting a spinal cord stimulator lead to the power source.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
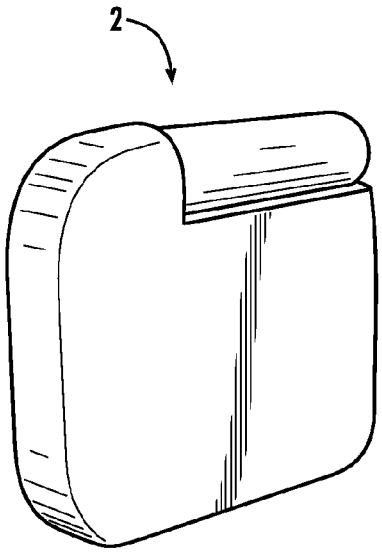
Prior Art Fig. 1
FIG. 1 shows a perspective view of a prior art power source for spinal cord stimulation.
Figure 2:
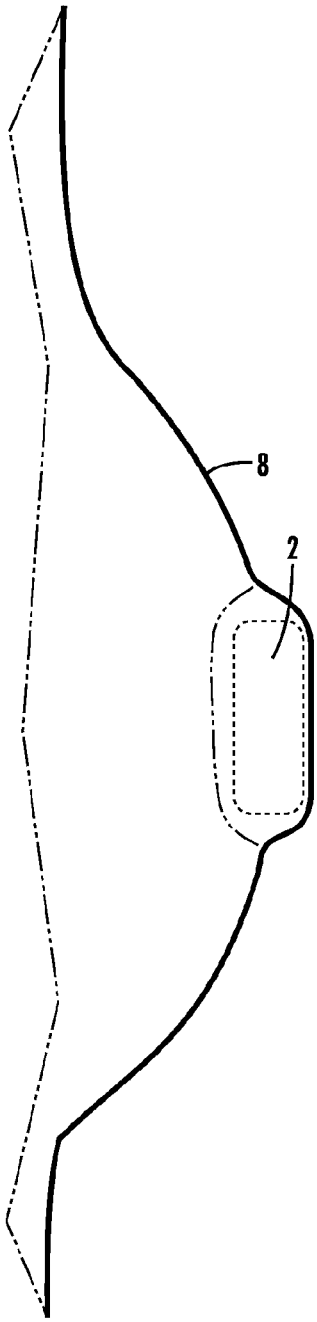
Prior Art Fig. 2
FIG. 2 shows a side view of the power source of FIG. 1 as implanted in a patient's buttock.
Figure 3:
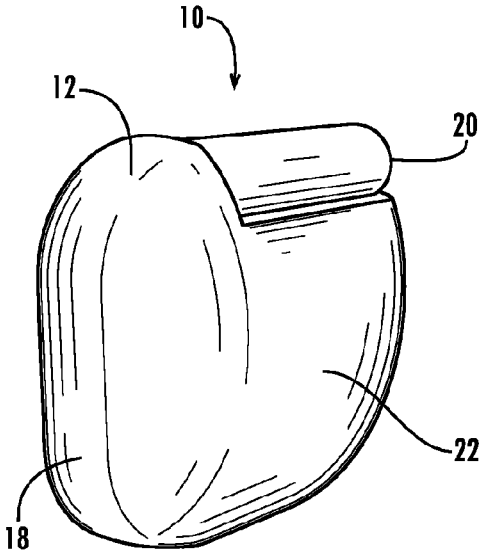
FIG. 3 shows a perspective view of a power source for spinal cord stimulation in accordance with an example embodiment of the present invention.
Figure 4:
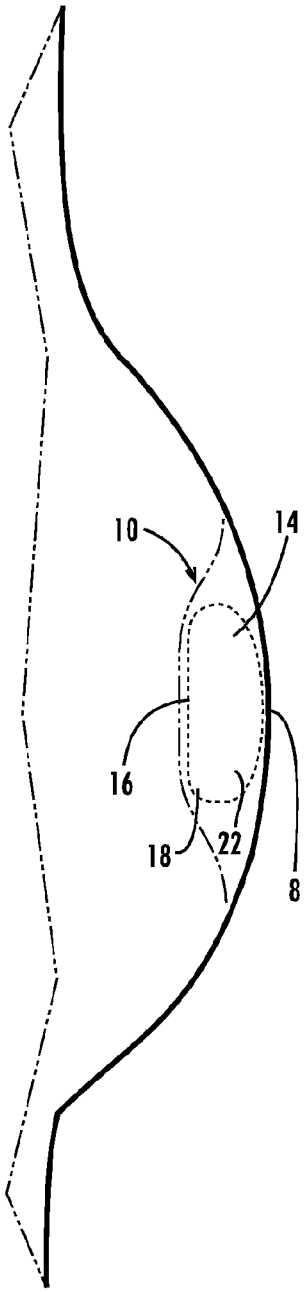
FIG. 4 shows a side view of the power source of FIG. 3 as implanted in a patient's buttock.

With reference now to the drawing figures, FIGS. 3 and 4 show an improved power source 10 for spinal cord stimulation. Currently commercially available power sources include those marketed under the ANS Genesis® and EON™ labels and the Medtronic Itrel®, Restore® and Synergy™ labels, all of which are well known in the industry and which internal electronics are also well known, and any of which can be adapted with an improvement of the present invention. The user activates the power source 10 with an external controller so that the power source delivers pulses of energy at the user's discretion, the process of which is also generally well known in the art.

Preferably, the power source 10 includes a generally puck-like housing or casing 12 formed of an inert and biocompatible material, such as titanium or a titanium alloy, although those skilled in the art will understand that the casing 12 can be formed of other inert and biocompatible materials. The casing 12 itself has an anterior face 14 that when implanted is adjacent (or closest to) the patient's skin and a posterior face 16 with at least one edge 18 between the anterior and posterior faces so as to form a generally enclosed structure or container for housing the internal electronics. In the depicted embodiment, the casing 12 has a generally rectangular profile with rounded corners, although those skilled in the art will understand that the casing 12 can be constructed of various shapes and sizes, as generally well known in the art. In an example embodiment, the faces 14 and 16 can have dimensions of about 50 to 60 millimeters long and 50 to 70 millimeters wide, while the edge can have width of about 10 to 20 millimeters, although those skilled in the art will understand that the power source can be larger or smaller.

Preferably, the anterior face 14 is convex or bowed outwardly or otherwise shaped so as to provide a profile or contour generally conforming to the profile of the patient's buttock 8 (or other contoured body part) or to otherwise minimize the edges of the power source. Additionally, the convex anterior face can be generally barrel vault shaped (as depicted in FIG. 3), domed shaped or semispherical, or any other shape that is generally bowed outwardly.

Optionally, the casing 12 can be formed of a flexible material and/or can have a concave posterior surface and a convex anterior surface so as to generally conform to the gluteal muscle. Additionally, the power source 10 includes at least one port 20 for receiving a lead from an implantable medical device so as to energize the lead. For example, the port 20 can receive an end of a spinal cord stimulator lead having electrodes thereon that is implanted in the epidural space.

In an alternative embodiment, a sheet or layer 22 formed of any biocompatible and inert material, such as a polymer layer, is applied to the anterior surface 16 of the casing 12 to create a contoured anterior surface. Also preferably, the layer is non-biodegradable. Suitable biocompatible materials for the layer can include, but are not limited to, polyurethane, polystyrene, polyvinylchloride, polyacrylates, silicone, silicone rubbers, silicone elastomers, silicone gel, polymers of ethylene-vinyl acetates and other acyl substituted cellulose acetates, polyvinyl flouride, poly(vinyl imidazole), chlorosulphonate polyolefins, polyethylene oxide, and homopolymer or copolymer blends thereof.

Preferably, the layer 22 has a smoothly-curved exterior profile, such as a convex profile, with no significant sharp edges or corners, so as to create a contour or an effect that would diminish the noticeability of the power source 10 when it is implanted beneath the user's skin in the buttock 8. The contour provided by the layer 22 on the anterior surface 16 can generally conform to the contour of a person's buttock 8, as shown in FIG. 4. In an example embodiment, the layer 22 can be about a millimeter thick at the casing's edge to about a few centimeters thick at the casing's center. In another example embodiment, the layer 22 can be about a millimeter thick at the casing's edge to about 1 centimeter thick at the casing's center. Those skilled in the art will also understand how to apply or bond the layer 22 to the casing 12 of power source 10 using an adhesive coating or a conventional bond agent.

Figure 5:
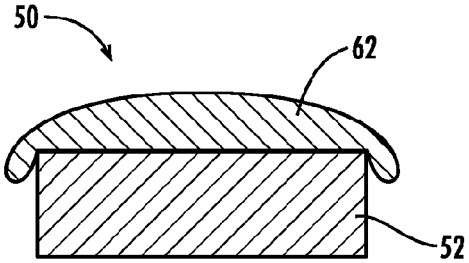
FIG. 5 shows a sectional view of a power source in accordance with another example embodiment of the present invention.

Alternatively or additionally, in another embodiment the layer 62 can extend beyond the edges of the casing 52 of the power source 50 so as to provide a tapering effect, as depicted in FIG. 5. Thus by tapering the layer 62 beyond the edges of the casing 52 of the power source 50, the edges of the power source will not appear as prominent under the patient's skin. Those skilled in the art will understand that the casing 52 and the power source 50 can take the form of various other shapes and sizes so as to minimize the appearance of the power source beneath the user's skin and be within the scope of the present invention.

Alternatively, the layer or sheet 22 can be a contoured cap or cover that fits over the power source 10. The cap can fit over the power source 10 and around the edge 18 such that the cap cinches or otherwise attaches or adheres to the power source. Alternatively, the layer or sheet 22 can comprise a fitted sleeve that fits around the power source (such as with an elastic material or otherwise). Still alternatively, the power source can be implanted within a pocket created within a cosmetic gluteal implant.

Generally, the power source 10 is a replaceable battery that is surgically replaced at roughly 3-5 years, although this time varies depending on how much the battery is used. Thus, preferably, the layer 22 of the power source does not bond too much to the surrounding tissue so that the implanted power source can be removed relatively easily, and a new power source can be implanted as needed. Alternatively, the power source 10 can be a rechargeable battery that is recharged by transferring energy through radio frequency. Still alternatively, the power source 10 can be a radiofrequency (RF) receiver having an antenna and internal electronics for receiving RF waves from an external RF transmitter and delivering the RF waves to the medical device.

Those skilled in the art will also understand that the power source 10 of the present invention can be used with other medical devices, in addition to spinal cord stimulators. For example, a layer 22 can be applied to a power source to be used with implantable medical devices such as muscle stimulators, drug delivery pumps, pacemakers, etc. The contour of the layer 22 can be adjusted to conform to the shape of the body part adjacent the power source 10 and to the shape and size of the respective power source.

Figure 6:
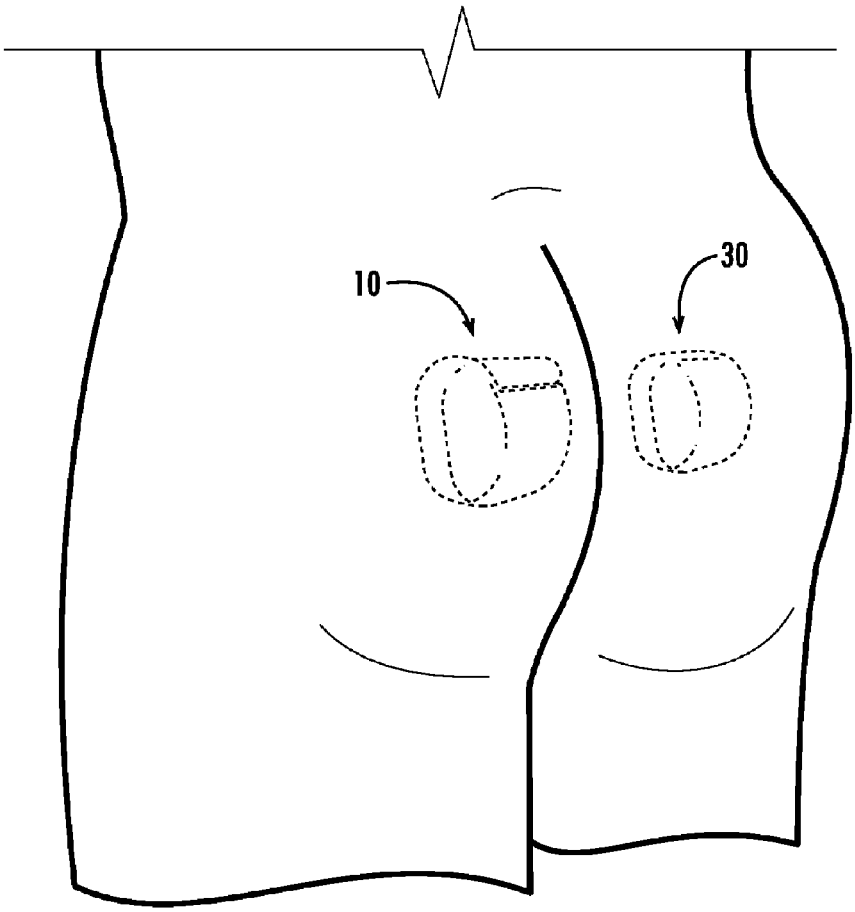
FIG. 6 shows a perspective view of the power source of FIG. 3 along with a cosmetic implant of substantially the same size and shape as the power source implanted into a patient's buttocks.

The present invention also includes a kit for spinal cord stimulation including a spinal cord stimulator lead, which can be a percutaneous lead or a surgical, paddle-type lead, and a power source 10 having a layer 22 thereon for providing a contour generally conforming to the contour of a person's buttocks. Optionally, the kit can also include a buttock or cosmetic gluteal implant 30 of a substantially similar size and shape as the power source 10 with contoured layer 22 on its anterior surface 16, as shown in FIG. 6. The cosmetic implant can be made of any biocompatible and inert material, such as a silicone or silicone gel, although those skilled in the art will understand that various other biocompatible and inert materials can be employed as well and will also understand how to construct a suitable cosmetic implant. By providing an implant of comparable size and shape as the power source 10, the power source 10 can be implanted into one buttock and the gluteal implant 30 can implanted in the other so as to create a balance. Alternatively, the kit can include a second power source substantially similar to the power source 10, so that one power source is implanted in each of the patient's buttocks and is each used to energize one or more leads.

The present further includes a method of implanting the power source 10 into a human or animal subject. The method includes the steps of implanting the power source 10 into one of a patient's buttocks at a predetermined height, depth, and lateral distance from the patient's spinal column and implanting a cosmetic gluteal implant 30 of substantially the same size and shape as the power source into the other of the patient's buttocks at substantially the same height, depth, and lateral distance from the patient's spinal column as the implanted power source so as to create a balanced look. The method can further include the step of connecting a spinal cord stimulator lead or other lead to the power source.

While the invention has been described with reference to preferred and example embodiments, it will be understood by those skilled in the art that a variety of modifications, additions and deletions are within the scope of the invention, as defined by the following claims.

What is claimed is:

1. A housing for a power source for supplying power to a medical device, wherein the housing is to be implanted in a contoured buttock of a human or animal subject, comprising:

an anterior portion of the housing with a contour generally conforming to the contour of the buttock, wherein the contoured anterior portion is substantially rigid;

a posterior portion of the housing; and at least one edge between the anterior and posterior portions of the housing, wherein the contoured anterior portion of the housing, the posterior portion of the housing, and the at least one edge form a generally enclosed structure.

2. The housing of claim 1, further comprising a port for receiving an end of a spinal cord stimulator lead.

3. The housing of claim 1, wherein the contour of the anterior portion is convex.

4. The housing of claim 1, wherein the contoured anterior portion comprises a biocompatible metal or metal alloy.

5. The housing of claim 1, wherein the contoured anterior portion comprises titanium or titanium alloy.

6. An improvement for a power source for spinal cord stimulation, wherein the power source includes a casing with an anterior portion, the power source being implantable into a contoured buttock, the improvement comprising:

a contoured anterior portion of the casing which generally conforms to the contoured buttock, wherein the contoured anterior portion of the casing is substantially rigid.

7. The improvement of claim 6, further comprising a cosmetic implant of substantially the same size and shape as the power source to be implanted in the human subject's other buttock.

*8. The improvement of claim 6, further comprising a layer of a biocompatible and inert material for creating the contoured anterior surface.*

*9. The improvement of claim 8, wherein the layer comprises a polymer layer.*

*10. The improvement of claim 6, further comprising a layer of a biocompatible and inert material that fits onto the casing to become a part of the casing and that defines the contoured anterior surface.*

*11. The improvement of claim 10, wherein the layer fits around at least one edge of the casing such that the layer attaches to the casing.*

*12. The improvement of claim 11, wherein the layer forms a cap that fits over the casing.*

*13. An attachment for a power source for a medical device, the power source implantable into a contoured buttock of a human or animal subject and including a casing, the casing having an anterior surface, the attachment comprising:*

*a layer of a biocompatible and inert material that attaches to the casing, the layer defining an anterior surface having a smoothly-curved, generally convex contour, the layer anterior-surface contour generally conforming to the contour of the buttock, wherein the layer anterior surface is substantially rigid.*

*14. The attachment of claim 13, wherein the layer fits around at least one edge of the casing to attach to the casing.*

*15. The attachment of claim 13, wherein the layer forms a cap that fits over the casing.*

*16. The attachment of claim 13, wherein the layer substantially covers the anterior surface of the casing.*

*17. The attachment of claim 13, wherein the biocompatible and inert material comprises a polymer.*

*18. The attachment of claim 13, wherein the biocompatible and inert material comprises a biocompatible metal or metal alloy.*

*19. The attachment of claim 13, wherein the power source is for spinal cord stimulation.*

*20. The attachment of claim 19, wherein the layer defines a port for receiving an end of a spinal cord stimulator lead.*

* * * * *